(12) United States Patent
Chervitz et al.

(10) Patent No.: US 6,960,213 B2
(45) Date of Patent: Nov. 1, 2005

(54) APPARATUS AND METHOD FOR ORTHOPEDIC FIXATION

(75) Inventors: Alan Chervitz, Palm Harbor, FL (US); T. Wade Fallin, Hyde Park, UT (US); Robert W. Hoy, Logan, UT (US)

(73) Assignee: MedicineLodge, Inc., Logan, UT (US)

( * ) Notice: Subject to any disclaimer, the term of this patent is extended or adjusted under 35 U.S.C. 154(b) by 217 days.

(21) Appl. No.: 09/981,927

(22) Filed: Oct. 17, 2001

(65) Prior Publication Data

US 2002/0177853 A1 Nov. 28, 2002

Related U.S. Application Data

(63) Continuation-in-part of application No. 09/863,174, filed on May 23, 2001, now Pat. No. 6,520,965.

(51) Int. Cl.$^7$ ............................................... A61B 17/58
(52) U.S. Cl. ............................. 606/74; 606/70; 606/103
(58) Field of Search .......................... 606/74, 70, 103, 606/69, 60, 71, 72, 73, 75, 113, 151, 232, 144; 623/17.11, 17.16

(56) References Cited

U.S. PATENT DOCUMENTS

| | | | |
|---|---|---|---|
| 4,119,091 A | 10/1978 | Partridge | |
| 4,146,022 A | 3/1979 | Johnson et al. | |
| 4,263,904 A | 4/1981 | Judet | |
| 4,269,180 A | 5/1981 | Dall et al. | |
| 4,456,006 A | 6/1984 | Wevers et al. | |
| 4,473,068 A | 9/1984 | Oh | |
| 4,667,662 A | 5/1987 | Titone | |
| 4,889,110 A | 12/1989 | Galline et al. | |
| 4,988,351 A | 1/1991 | Paulos et al. | |
| 5,129,902 A | 7/1992 | Goble et al. | |
| 5,190,545 A * | 3/1993 | Corsi et al. ................... | 606/74 |
| 5,324,291 A | 6/1994 | Ries et al. | |
| 5,415,658 A | 5/1995 | Kilpela et al. | |
| D373,632 S | 9/1996 | Price et al. | |
| 5,607,430 A | 3/1997 | Bailey | |
| 5,665,088 A | 9/1997 | Gil et al. | |
| 5,665,089 A * | 9/1997 | Dall et al. ..................... | 606/71 |
| 5,697,934 A | 12/1997 | Huebner | |
| 5,702,399 A | 12/1997 | Kilpela et al. | |
| 5,718,706 A | 2/1998 | Roger | |
| 5,741,259 A | 4/1998 | Chan | |
| 5,752,959 A | 5/1998 | Korhonen | |
| 5,772,663 A | 6/1998 | Whiteside et al. | |
| 5,797,915 A | 8/1998 | Pierson, III et al. | |
| 5,797,916 A | 8/1998 | McDowell | |
| 5,810,824 A * | 9/1998 | Chan ........................... | 606/70 |
| D404,128 S | 1/1999 | Huebner | |
| 5,935,133 A | 8/1999 | Wagner et al. | |
| 5,941,881 A | 8/1999 | Barnes | |
| 5,964,769 A | 10/1999 | Wagner et al. | |
| 5,993,449 A * | 11/1999 | Schlapfer et al. ............. | 606/60 |
| 5,993,452 A | 11/1999 | Vandewalle | |
| 6,053,921 A * | 4/2000 | Wagner et al. ................ | 606/74 |
| 6,068,648 A * | 5/2000 | Cole et al. ................... | 606/232 |
| 6,086,590 A | 7/2000 | Margulies et al. | |
| 6,120,505 A * | 9/2000 | Huebner ....................... | 606/74 |
| 6,520,965 B2 * | 2/2003 | Chervitz et al. .............. | 606/74 |
| 6,544,267 B1 * | 4/2003 | Cole et al. ................... | 606/74 |

OTHER PUBLICATIONS

Muller et al., Manual Of Internal Fixation, Techniques Recommended by the AO Group, Second Edition, Springer Verlag, Berlin Heidelberg, New York, 1979, pp. 42–47, 70–71, and 248–253.

* cited by examiner

*Primary Examiner*—Pedro Philogene
(74) *Attorney, Agent, or Firm*—Pandiscio & Pandiscio

(57) ABSTRACT

A filament retaining washer for mounting about the shank of a bone screw deployed in a bone whereby to retain the filament to the bone, the filament retaining washer comprising a structure having a screw hole extending therethrough for receiving therein the shank of the bone screw deployed in the bone, whereby to secure the structure to the bone, the screw hole defining a first axis, and the structure having a filament hole extending therethrough for receiving a filament therein so as to retain the filament to the structure, the filament hole defining a second axis extending substantially perpendicular to the first axis.

44 Claims, 26 Drawing Sheets

APPARATUS AND METHOD FOR ORTHOPEDIC FIXATION

REFERENCE TO PENDING PRIOR PATENT APPLICATION

This application is a continuation-in-part of U.S. patent application Ser. No. 09/863,174, filed May 23, 2001 now U.S. Pat. No. 6,520,965 by T. Wade Fallin et al. for APPARATUS AND METHOD FOR ORTHOPEDIC FIXATION which patent application is hereby incorporated herein by reference.

FIELD OF THE INVENTION

This invention relates to surgical apparatus and methods in general, and more particularly to surgical apparatus and methods for fixing bone and soft tissue in place during trauma and reconstructive surgery.

BACKGROUND OF THE INVENTION

Bone fixation, sometimes also referred to as fracture fixation, is an established art. Fixation screws, and fixation screws in combination with metal plates, are widely used in the art to stabilize bone so as to facilitate healing.

Surgical cables, and surgical cables in combination with metal plates, are also well known in the bone fixation art. Cables, and cables in combination with plates, are generally used in situations where the use of screws, or screws in combination with plates, is not suitable. By way of example, cables, and cables in combination with plates, are frequently used in the fixation of long oblique fractures resulting from high energy trauma such as a motor vehicle accident. By way of further example, screw fixation is frequently not adequate for fractures that are highly comminuted, and fixation with cables, or cables in combination with plates, is required.

Cables are also sometimes used in conjunction with screws, and in conjunction with screws in combination with plates. By way of example, cables may be used in conjunction with screws, and screws in combination with plates, where a screw strips its threads in deployment, or where screws, or screws in combination with plates, are deemed insufficient for the fixation at hand.

With cable fixation, it is customary to encircle the subject bone with the body of the cable, and then to secure the two free ends of the cable together with a deformable crimp so as to effect fixation.

In general, cable fixation on the shaft of a so-called "long bone" does not present a significant problem with migration, inasmuch as this portion of the bone is substantially tubular in geometry. However, the ends of these long bones typically have a significant flare in their geometry. As a result, tightening of the encircling cable often causes the cable (and crimp) to migrate toward the narrower section of the bone. Such migration can displace the cable sufficiently far from its intended location as to significantly loosen, or render ineffective, encirclement of the bone segments.

Thus, there is a need for an improved apparatus and method which will permit bone fixation to be effected with screws and cable.

There further exists a need for an improved apparatus and method for effecting bone fixation with cable, such that the cable will not slide along the bone during tightening of the cable.

In addition to the foregoing, in many situations, soft tissue may need to be attached to bone. By way of example, a ligament may need to be attached to bone during trauma and reconstructive surgery. In some of these situations, bone fixation may also be necessary, and such bone fixation may involve the use of screws, and/or cables and plates, either alone or in combination with one another.

Thus, there is a need for an improved apparatus and method for attaching soft tissue to bone.

There further exists a need for an improved apparatus and method for attaching soft tissue to bone, where screws may be used to help effect fixation to bone.

SUMMARY OF THE INVENTION

Accordingly, one object of the present invention is to provide improved apparatus for use in bone fixation.

Another object of the present invention is to provide improved apparatus for use in bone fixation which involves the use of bone screws, metal plates and/or cables.

Still another object of the present invention is to provide an improved method for bone fixation.

Yet another object of the present invention is to provide improved apparatus for attaching soft tissue to bone.

And another object of the present invention is to provide improved apparatus for attaching soft tissue to bone, where screws may be used to help effect fixation to bone.

A further object of the present invention is to provide an improved method for attaching soft tissue to bone.

These and other objects of the present invention are addressed by the provision and use of a novel filament retaining washer for mounting about the shank of a bone screw deployed in a bone whereby to retain the filament to the bone, the filament retaining washer comprising a structure having a screw hole extending therethrough for receiving therein the shank of the bone screw deployed in the bone, whereby to secure the structure to the bone, the screw hole defining a first axis, and the structure having a filament hole extending therethrough for receiving a filament therein so as to retain the filament to the structure, the filament hole defining a second axis extending substantially perpendicular to the first axis, with the second axis being aligned with a bone screw extending through the screw hole.

In another form of the invention, there is provided a filament retaining washer for mounting about the shank of a bone screw deployed in a bone whereby to retain the filament to the bone, the filament retaining washer comprising a body; a downwardly projecting extension connected to the body and having a screw hole extending therethrough for receiving therein the shank of the bone screw deployed in the bone, whereby to secure the downwardly projecting extension to the bone, the screw hole defining a first axis; and an upwardly projecting extension connected to the body and having a filament hole extending therethrough for receiving a filament therein so as to retain the filament to the upwardly projecting extension, the filament hole defining a second axis extending substantially perpendicular to the first axis, with the second axis being aligned with a bone screw extending through the screw hole.

And in another form of the invention, there is provided a system for securing an object to a bone, the system comprising a bone screw; a washer comprising a body, a downwardly projecting extension connected to the body and having a screw hole extending therethrough for receiving therein the shank of the bone screw deployed in the bone, whereby to secure the downwardly projecting extension to the bone, the screw hole defining a first axis, and an upwardly projecting extension connected to the body and having a filament hole extending therethrough, for receiving a filament therein so as to retain the filament to the upwardly projecting extension, the filament hole defining a second axis extending substantially perpendicular to the first axis, with the second axis being aligned with a bone screw extending through the screw hole; and a filament received by the filament hole, the filament securing the object to the bone.

In another form of the invention, there is provided a method for securing an object to a bone, the method comprising providing a screw, a filament and a suture retaining washer, the suture retaining washer comprising a body, a downwardly projecting extension connected to the body and having a screw hole extending therethrough for receiving therein the shank of a bone screw deployed in the bone, whereby to secure the downwardly projecting extension to the bone, the screw hole defining a first axis, and an upwardly projecting extension connected to the body and having a filament hole extending therethrough for receiving a filament therein so as to retain the filament to the upwardly projecting extension, the filament hole defining a second axis extending substantially perpendicular to the first axis, with the second axis being aligned with a bone screw extending through the screw hole; securing the washer to the bone with the screw, with the filament extending through the filament hole; and using the filament to secure the object to the bone.

And in another form of the invention, there is provided a method for securing an object to a bone, the method comprising providing a screw, a filament and a suture retaining washer, the suture retaining washer comprising a structure having a screw hole extending therethrough for receiving therein the shank of the bone screw deployed in the bone, whereby to secure the structure to the bone, the screw hole defining a first axis, and the structure having a filament hole extending therethrough for receiving a filament therein so as to retain the filament to the structure, the filament hole defining a second axis extending substantially perpendicular to the first axis, with the second axis being aligned with a bone screw extending through the screw hole; securing the washer to the bone with the screw, with the filament extending through the filament hole; and using the filament to secure the object to the bone.

In another form of the invention, there is provided a filament retaining washer for mounting about the shank of a bone screw deployed in a bone whereby to retain the filament to the bone, the filament retaining washer comprising: a body; a downwardly projecting extension connected to the body and having a screw hole extending therethrough for receiving therein the shank of the bone screw deployed in the bone, whereby to secure the downwardly projecting extension to the bone, the screw hole defining a first axis; and an upwardly projecting extension connected to the body and having a filament hole extending therethrough for receiving a filament therein so as to retain the filament to said upwardly projecting extension, the filament hole defining a second axis extending substantially perpendicular to the first axis, with the upwardly projecting extension being displaced laterally and longitudinally from the downwardly projecting extension.

In another form of the invention, there is provided a filament retaining washer for mounting about the shank of a bone screw deployed in a bone whereby to retain the filament to the bone, the filament retaining washer comprising: a structure having a screw hole extending therethrough for receiving therein the shank of the bone screw deployed in the bone, whereby to secure the structure to said bone, the screw hole defining a first axis, and the structure having a filament hole so as to retain the filament to the structure, the filament hole defining a second axis extending substantially perpendicular to the first axis, with the second axis extending parallel to a third axis extending through the first axis.

The above and other features of the invention, including various novel details of construction and combinations of parts, will now be more particularly described with reference to the accompanying drawings and pointed out in the claims. It will be understood that the particular devices, assembly and method embodying the invention are shown by way of illustration only and not as limitations of the invention. The principles and features of this invention may be employed in various and numerous embodiments without departing from the scope of the invention.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
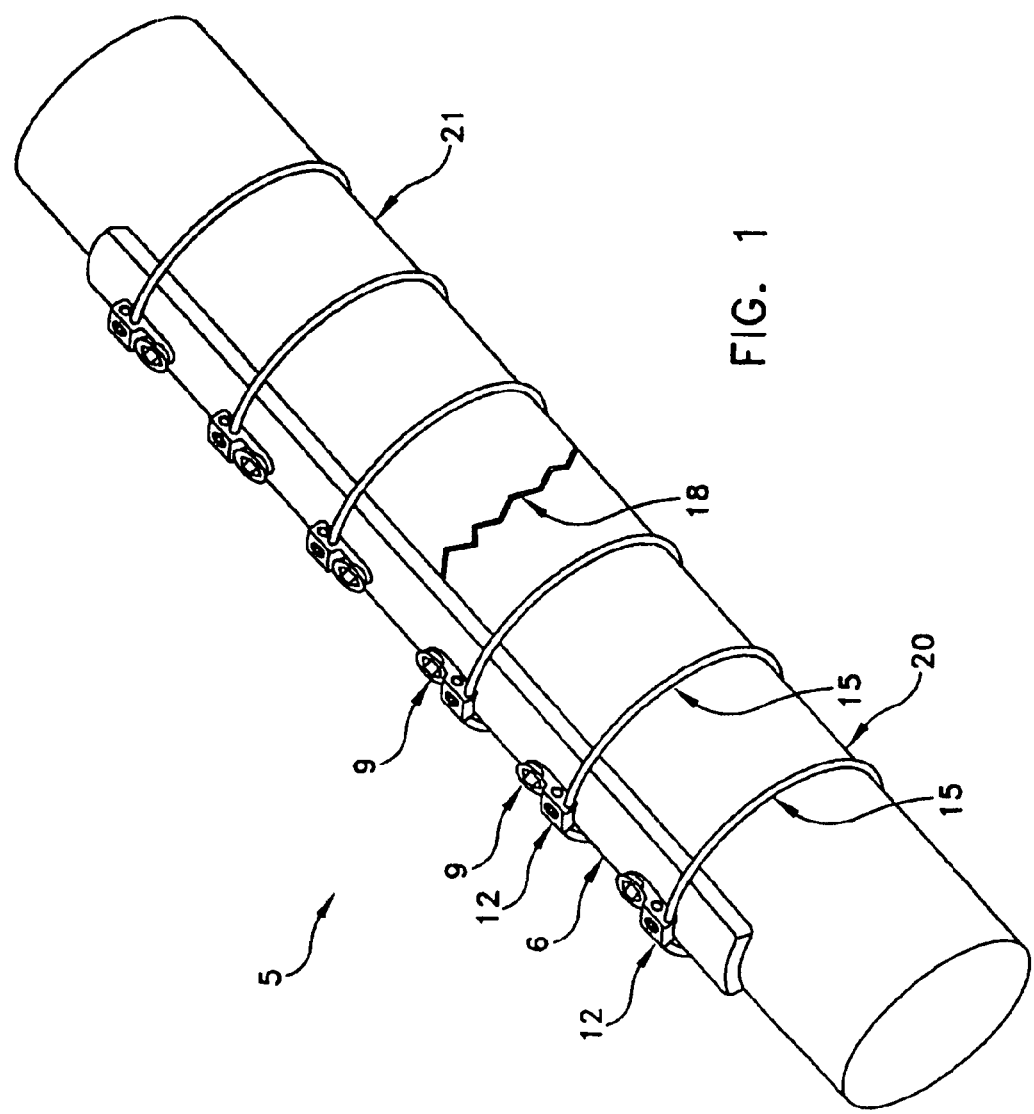
FIG. 1 is a perspective view showing a novel surgical fastening system securing together two bone segments.
Figure 2:
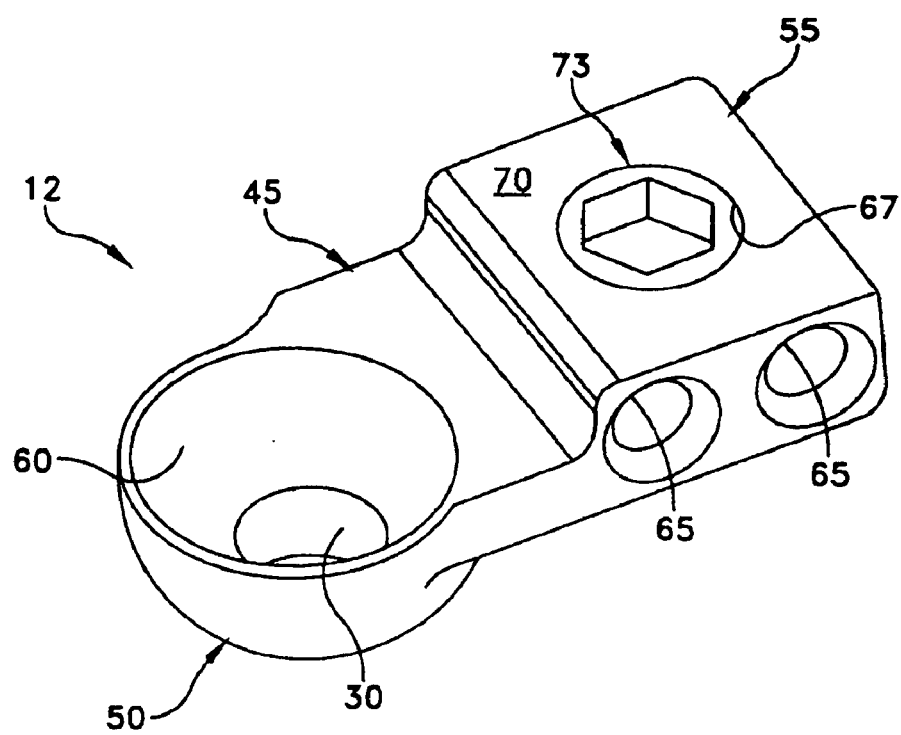
FIG. 2 is perspective view of a cable retaining washer which forms part of the surgical fastening system shown in FIG. 1.
Figure 3:
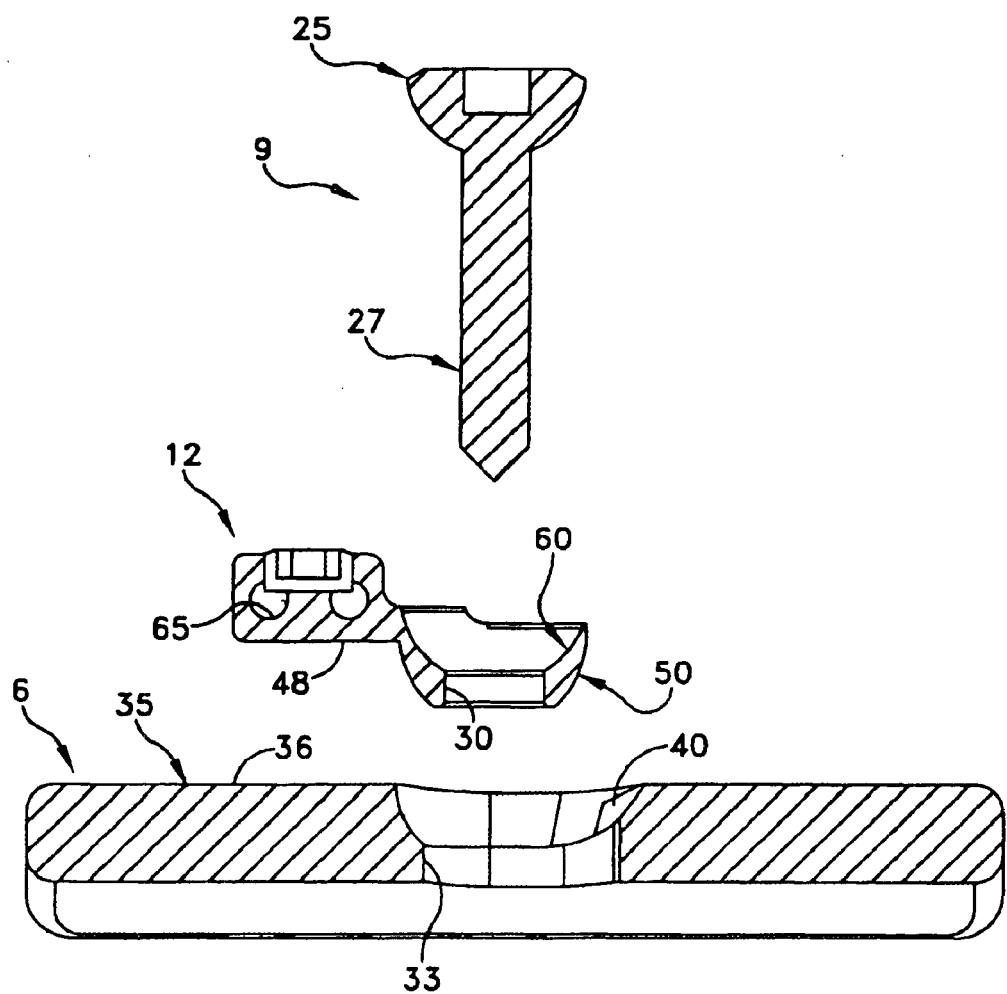
FIG. 3 is an exploded side view, in section, of a bone screw, cable retaining washer and bone plate which form part of the surgical fastening system shown in FIG. 1.

Looking first at FIGS. 1–3, there is shown a surgical fastening system 5 which comprises one preferred form of the invention.

Surgical fastening system 5 generally comprises a bone plate 6, a plurality of bone screws 9, a plurality of cable retaining washers 12, and a plurality of cable loops 15. As used herein, the term "cable" is intended to encompass braided cable, wire and the like.

Bone plate 6 is deployed so that the bone plate extends across the fracture line 18 of two bone segments 20, 21. The heads 25 (FIG. 3) of bone screws 9 engage cable retaining washers 12, while the shanks 27 of bone screws 9 extend through screw holes 30 in cable retaining washers 12, through screw holes 33 in bone plate 6 and into bone segments 20, 21, whereby to secure bone plate 6 to bone segments 20, 21 and, the in process, to secure bone segments 20, 21 together. Additionally, cable loops 15 encircle bone segments 20, 21 and are secured to cable retaining washers 12, whereby cable loops 15 further secure bone segments 20, 21 to bone plate 6 and, as a result, to one another.

Bone plate 6 is of the sort well known in the art. By way of example but not limitation, bone plate 6 generally comprises an elongated body 35 penetrated by the aforementioned screw holes 33. The bone plate's top surface 36 generally includes recesses 40 about the top ends of screw holes 33; in conventional bone plate applications, recesses 40 receive the semi-spherical undersides of the heads 25 of bone screws 9.

Bone screws 9 are also of the sort well known in the art. Bone screws 9 comprise the aforementioned head 25 and the aforementioned shank 27.

Cable restraining washer 12 comprises a body 45 having a bottom surface 48 (FIG. 3) for engaging the top surface 36 of bone plate 6, a downwardly projecting extension 50 for seating in a recess 40 in bone plate 6, and an upwardly projecting extension 55 for receiving and restraining at least one cable loop 15.

Downwardly projecting extension 50 preferably has a semi-spherical configuration similar to the semi-spherical underside of a head 25 of a bone screw 9 so as to seat in one of the recesses 40 commonly formed in bone plate 6.

A recess 60 is formed in body 45, in alignment with the downwardly projecting extension 50 and screw hole 30. Recess 60 is sized so as to receive the head 25 of a bone screw 9, and screw hole 30 is sized so as to receive the shank 27 of a bone screw 9. In this way, cable restraining washer 12 can be mounted to bone plate 6 so that the washer's downwardly projecting extension 50 seats in a recess 40 formed in bone plate 6, and a bone screw 9 may be passed through the cable retaining washer 12 so that the head 25 of the screw 9 is seated in the washer's recess 60 and so that the shank 27 of the bone screw 9 passes through the washer's screw hole 30, through the screw hole 33 formed in bone plate 6, and into a bone segment 20, 21, whereby to secure the cable retaining washer 12 and bone plate 6 to one another, and to a bone segment 20, 21.

Cable retaining washer 12 also comprises the upwardly projecting extension 55 for receiving and retaining one or more cable loops 15. More particularly, cable retaining washer 12 also comprises at least one cable hole 65 extending perpendicular to the axis of the washer's screw hole 30. Cable hole 65 is sized to slidingly receive a cable loop 15. A threaded set screw hole 67 extends downwardly from the top surface 70 of the washer's upwardly projecting extension 55. The bottom end of set screw hole 67 intersects the at least one cable hole 65 (FIG. 3). A set screw 73 is positioned in set screw hole 67. Set screw 73 may be tightened down so as to engage a cable loop 15 extending through a cable hole 65, whereby to secure that cable loop to the cable retaining washer 12 and, as a result, to secure that cable loop to a bone segment 20, 21.

Surgical fastening system 5 is intended to be used as follows.

First, bone plate 6 is positioned against bone segments 20, 21. Then bone screws 9 are used to secure cable retaining washers 12 and bone plate 6 to one another and to bone segments 20, 21. Next, cable loops 15 are passed through cable holes 65 in the cable retaining washers 12, and then set screws 73 are used to lock cable loops 15 to the washers.

Figure 4:
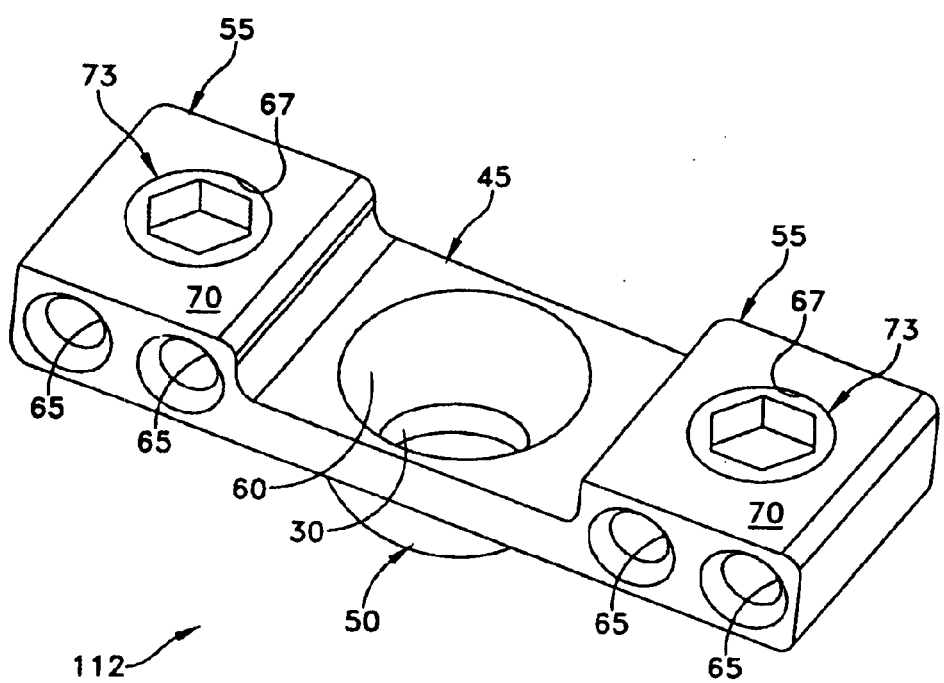
FIG. 4 is a perspective view of an alternate form of cable retaining washer formed in accordance with the present invention.

Looking next at FIG. 4, there is shown a cable retaining washer 112 which comprises an alternative form of the invention. Cable retaining washer 112 is substantially the same as the cable retaining washer 12 described above, except that it also includes a second upwardly projecting extension 55, along with that extension's associated cable holes(s) 65, set screw hole 67, and set screw 73.

Figure 5:
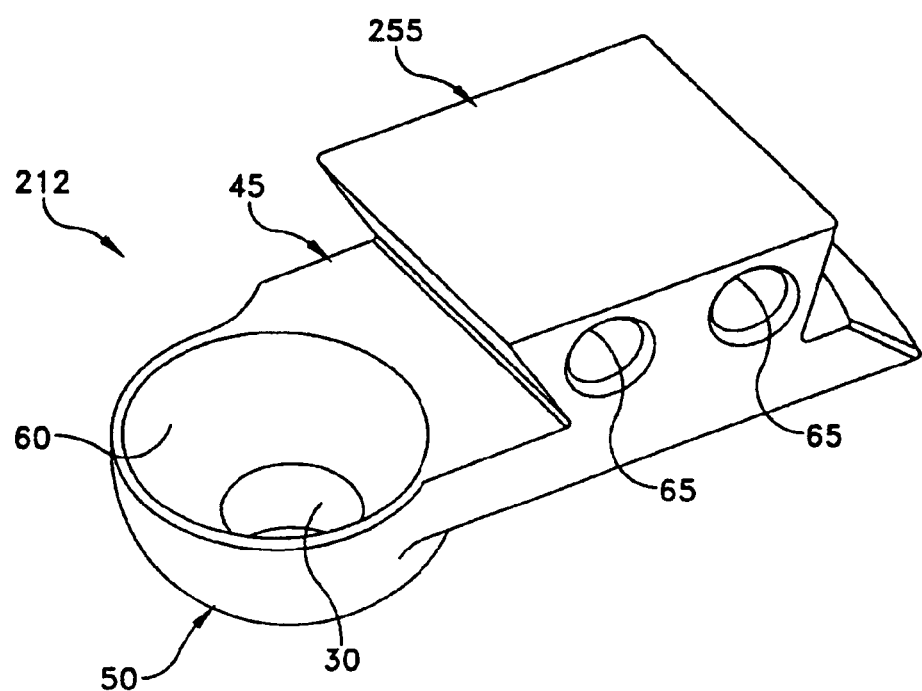
FIG. 5 is a perspective view of another alternative form of cable retaining washer formed in accordance with the present invention.

Looking next at FIG. 5, there is shown a cable retaining washer 212 which comprises another alternative form of the invention. Cable retaining washer 212 is substantially the same as the cable retaining washer 12 described above, except that its upwardly projecting extension 255 lacks the set screw hole 67 and set screw 73 for locking a cable loop 15 within a cable hole 65. Instead, with cable retaining washer 212, upwardly projecting extension 255 is formed so as to be crimpable, whereby to mechanically lock a cable loop 15 within a cable hole 65. In one preferred form of the invention, upwardly projecting extension 255 is formed with a trapezoidal cross-section such as that shown in FIG. 5, whereby to facilitate crimping of the upwardly extending projection 255 about the cable.

Figure 6:
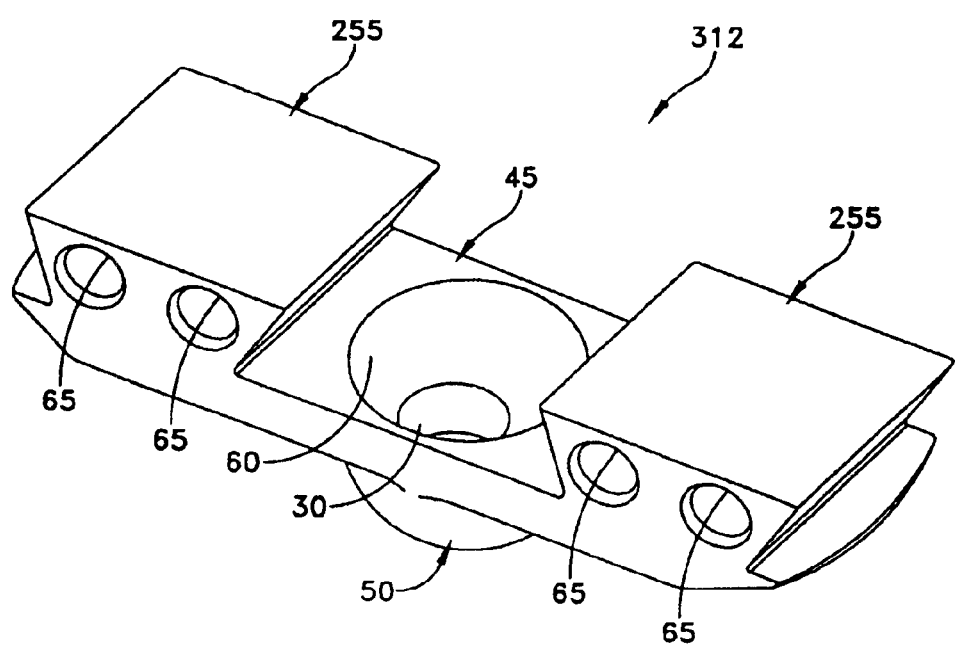
FIG. 6 is a perspective view of still another alternative form of cable retaining washer formed in accordance with the present invention.

Looking next at FIG. 6, there is shown a cable retaining washer 312 which comprises another alternative form of the invention. Cable retaining washer 312 is substantially the same as the cable retaining washer 212 described above, except that it includes a second upwardly projecting extension 255.

Figure 7:
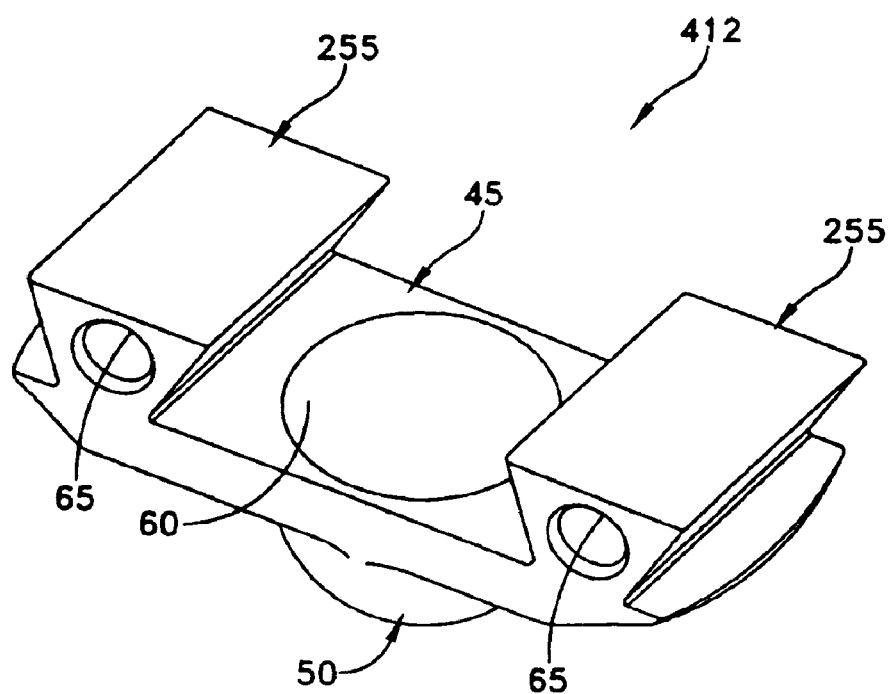
FIG. 7 is a perspective view of yet another alternative form of cable retaining washer formed in accordance with the present invention.

Looking next at FIG. 7, there is shown a cable retaining washer 412 which comprises another alternative form of the invention. Cable retaining washer 412 is substantially the same as the cable retaining washer 312 described above, except that each of the upwardly projecting extensions 255 has only one cable hole 65 formed therein.

In the cable retaining washers 12, 112, 212, 312 and 412 described above, the downwardly projecting extension 50 has a semi-spherical configuration so as to essentially replicate the semi-spherical underside of the head 25 of a bone screw 9, whereby it may be received in the recess 40 formed in bone plate 6. However, forming the downwardly projecting extension 50 with a semi-spherical configuration can sometimes result in the cable retaining washer turning somewhat about the axis of its screw hold 30 as bone screw 9 is screwed into a bone segment 20, 21. This can present an inconvenience to the surgeon.

Figure 8:
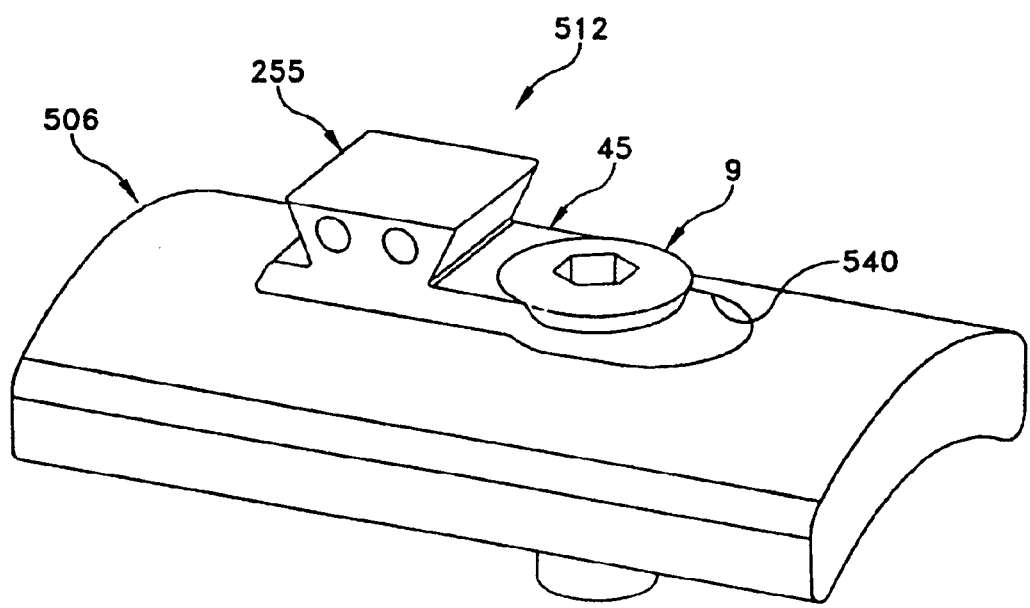
FIG. 8 is a perspective view of a bone screw, cable retaining washer and bone plate which comprise another embodiment of the present invention.
Figure 9:
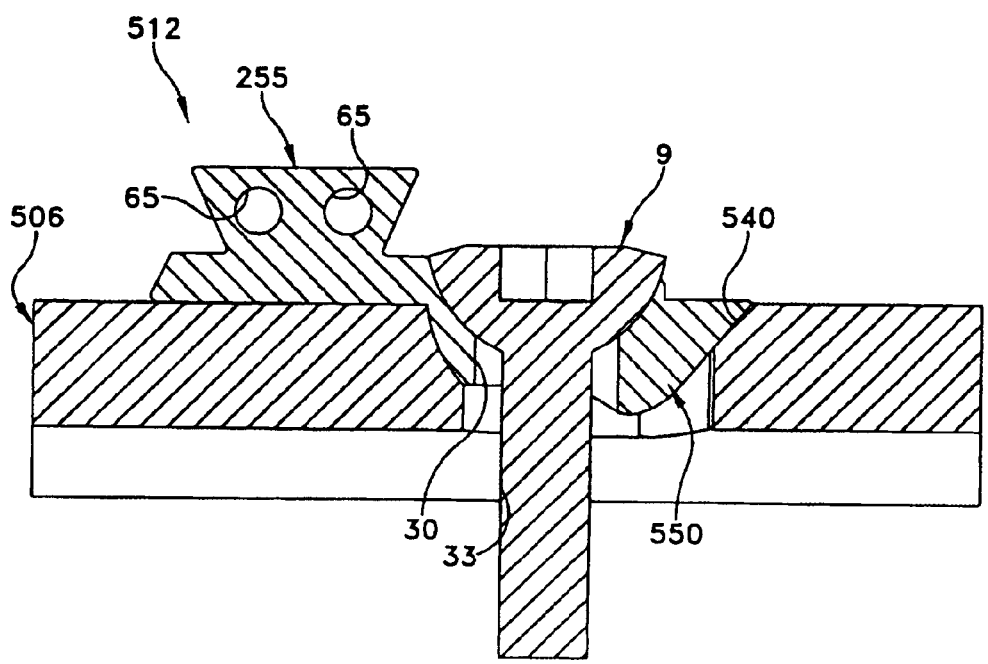
FIG. 9 is a side view, in section, of the apparatus shown in FIG. 8.

To guard against this, and looking now at FIGS. 8 and 9, there is shown a bone plate 506 which is provided with an elongated recess 540 and a cable retaining washer 512. Cable retaining washer 512 is substantially the same as the cable retaining washer 212 shown in FIG. 5, except that the downwardly projecting extension 50 of cable retaining washer 212 (FIG. 5) has been replaced with a downwardly projecting extension 550 having a cross-sectional profile matching that of the bone plate's elongated recess 540. If desired, the cable retaining washers 12, 112, 312, and 412 may also have their downwardly projecting extensions 50 replaced with similar downwardly projecting extensions 550, whereby they can mate securely with recesses 540 of a bone plate 506.

Figure 10:
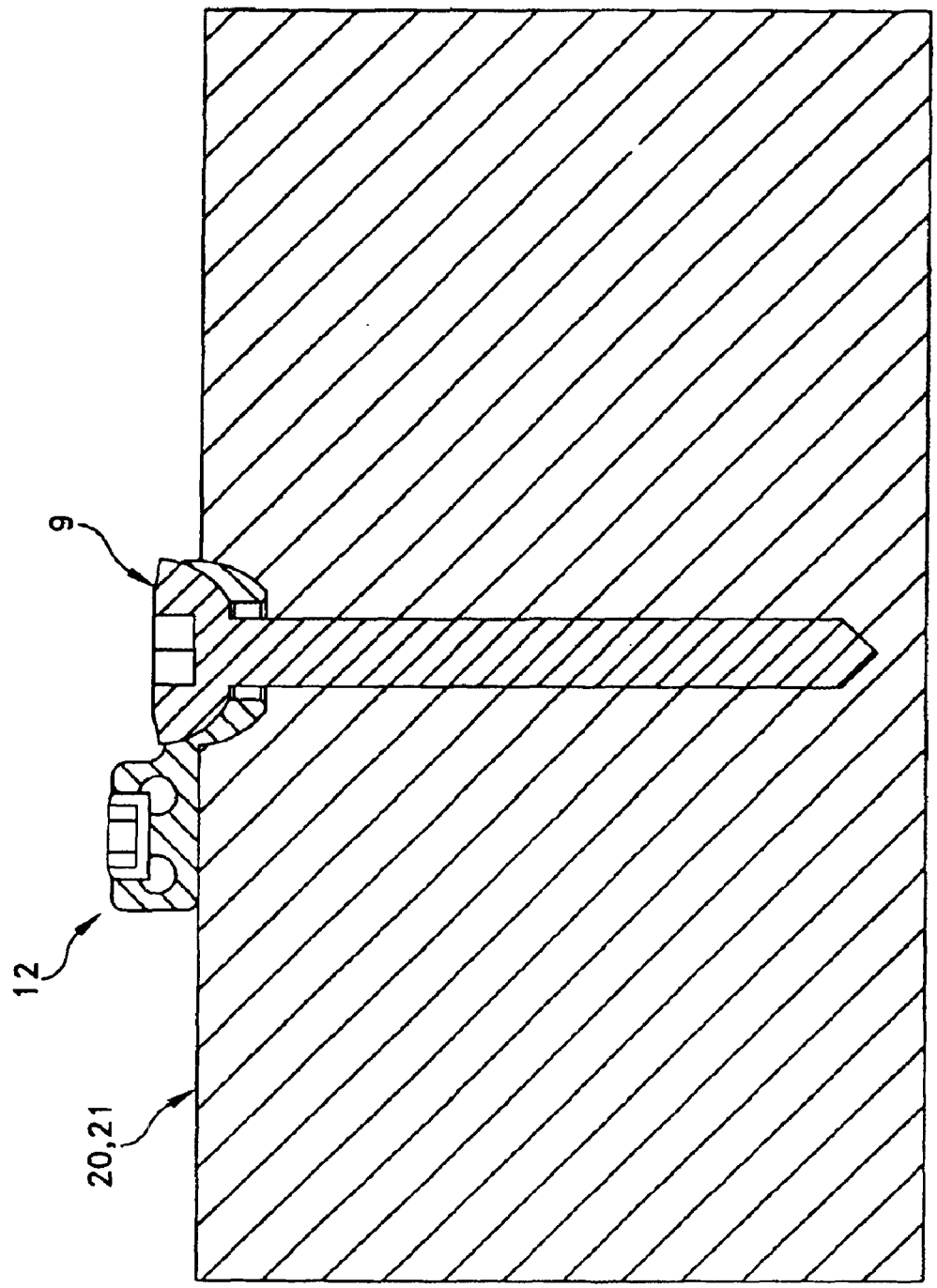
FIG. 10 is a side view, partially in section, showing a bone screw securing the cable retaining washer of FIG. 2 directly to a bone.

It is also possible to use the cable retaining washers of the present invention without a bone plate. In this case, the bone screw passes through the cable retaining washer and directly into a bone segment 20, 21. If desired, cable retaining washers 12, 112, 212, 312, 412 and/or 512 may be used in this way, with the downwardly projecting extensions bearing against, and generally penetrating into, bone segment 20, 21. See, for example, FIG. 10, where cable retaining washer 12 is shown engaging a bone segment 20, 21.

Alternatively, if desired, the bottom surface of the cable retaining washer can be modified so as to reduce, or entirely remove, the downwardly projecting extension.

Figure 11:
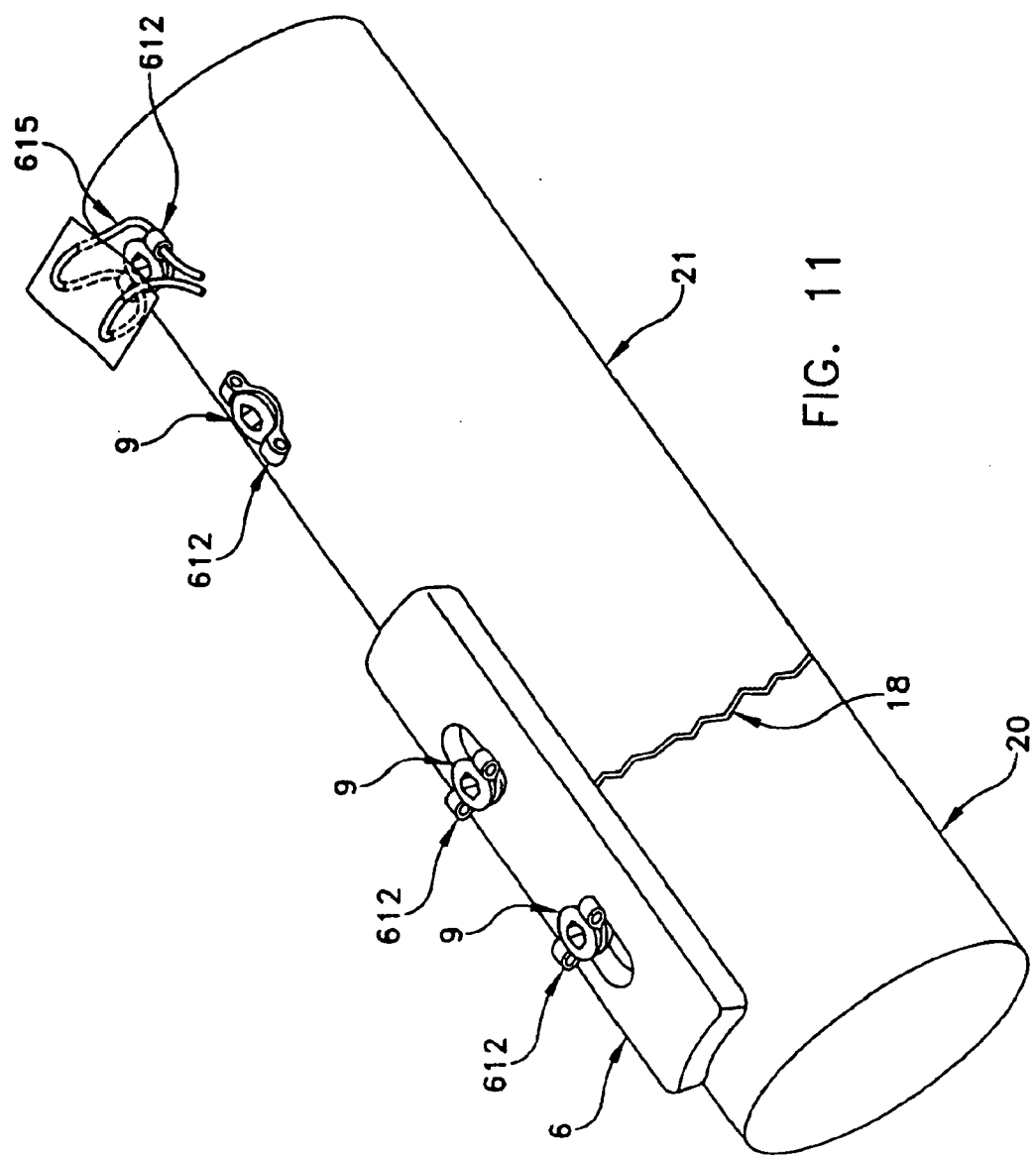
FIG. 11 is a perspective view showing an alternative form of surgical fastening system formed in accordance with the present invention.
Figure 12:
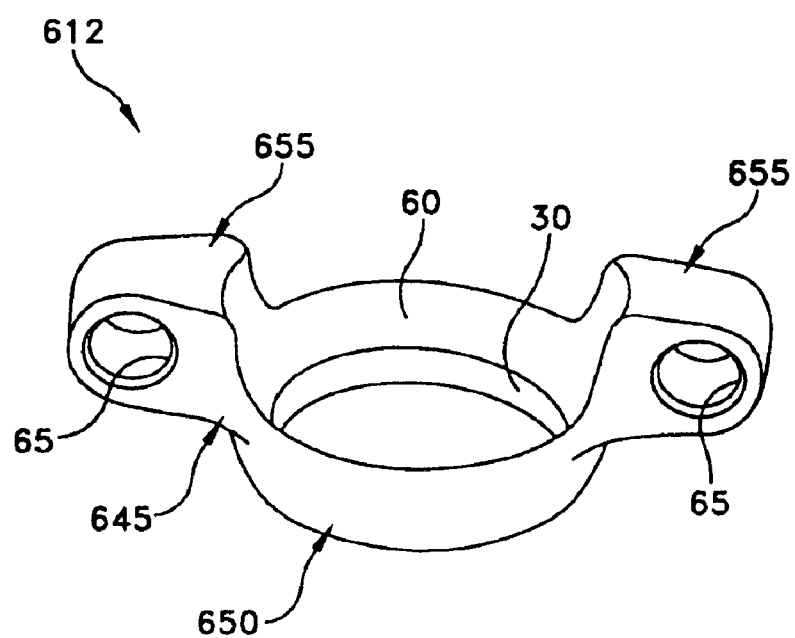
FIG. 12 is a perspective view of a suture retaining washer which forms part of the surgical fastening system shown in FIG. 11.
Figure 13:
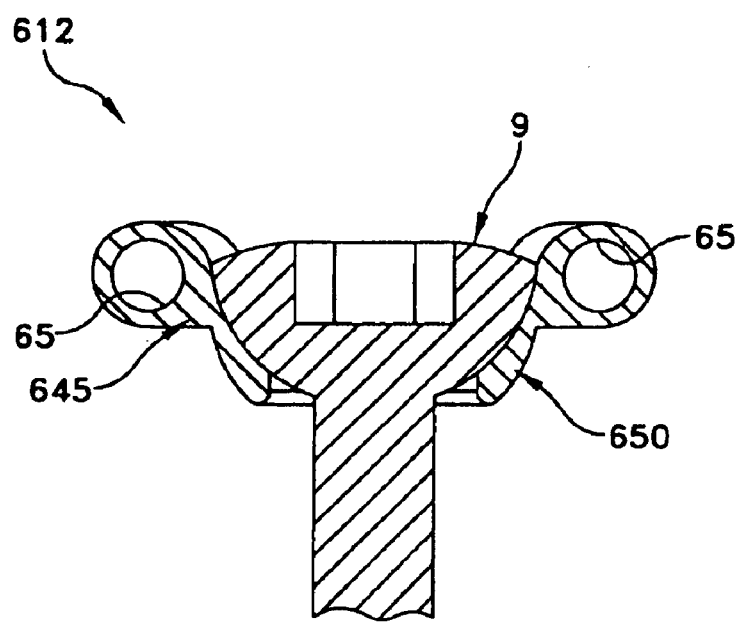
FIG. 13 is a partial sectional view of a bone screw and suture retaining washer which form part of the surgical fastening system shown in FIG. 11.

Looking next at FIGS. 11–13, there is shown a suture retaining washer 612 which comprises another form of the invention. Suture retaining washer 612 comprises a body 645. Suture retaining washer 612 also comprises a downwardly projecting extension 650 for seating in a recess 40 of a bone plate 6 or for engaging the outer surface of a bone segment 20, 21. Suture retaining washer 612 also comprises at least one upwardly projecting extension 655 for receiving and retaining at least one suture loop 615.

A screw hole 30 is formed in downwardly projecting extension 650 and a recess 60 is formed in body 645. Recess 60 is sized to receive the head 25 of a bone screw 9, and screw hole 30 is sized to receive the shank 27 of bone screw 9. In this way, suture retaining washer 612 can be mounted to bone plate 6 so that the downwardly projecting extension 650 seats in a corresponding recess 40 in bone plate 6, and a bone screw 9 may be passed through the suture retaining washer 612 so that the head 25 of the screw 9 is seated in the washer's recess 60 and the shank 27 of the bone screw 9 passes through the washer's screw hole 30, through the screw hole 33 in bone plate 6, and into a bone segment 20, 21, whereby to secure suture retaining washer 612 and bone plate 6 to one another, and to a bone segment 20, 21. Alternatively, suture retaining washer 612 can be mounted directly to a bone segment 20, 21 by seating downwardly projecting extension 650 against a bone segment 20, 21, and then passing a bone screw 9 through the suture retaining washer 612 so that the head 25 of the screw 9 is seated in the washer's recess 60 and the shank 27 of the bone screw 9 passes through the washer's screw hole 30 and into a bone segment 20, 21.

Suture retaining washer 612 also comprises at least one upwardly projecting extension 655 for receiving and retaining one or more loops 615. More particularly, suture retaining washer 612 also comprises at least one upwardly projecting extension 655, with each upwardly projecting extension having at least one suture hole 65 extending perpendicular to the axis of the washer's screw hole 30. Suture hole 65 is sized to slidingly receive a suture loop 615.

Figure 14:
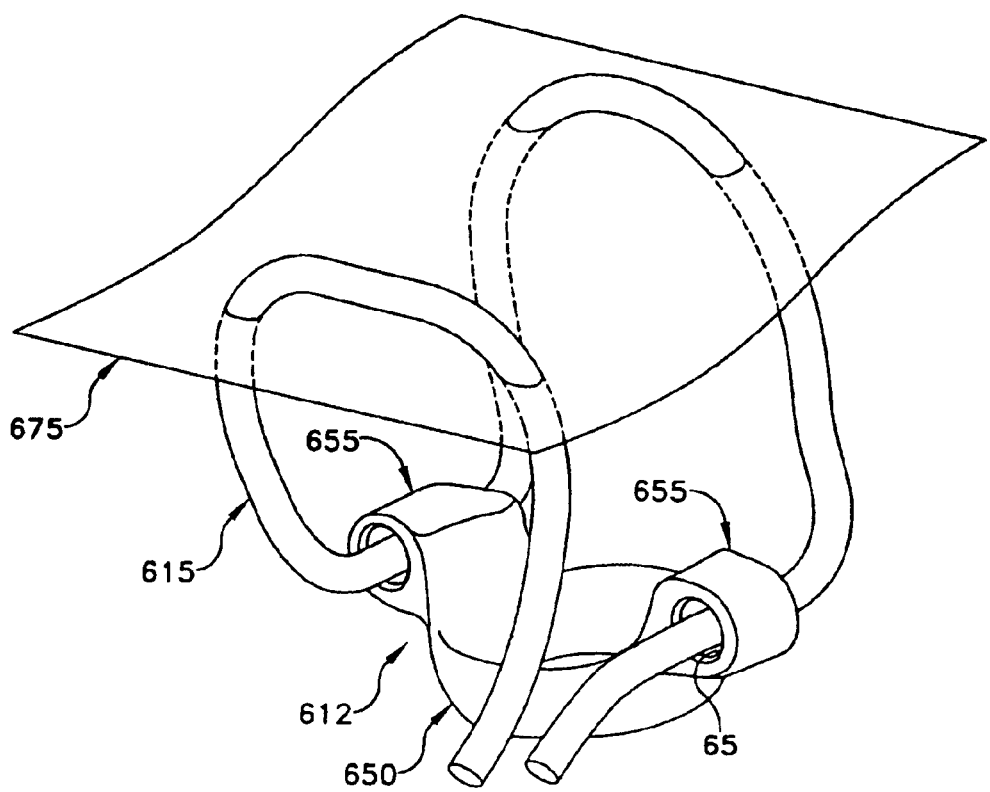
FIG. 14 is a perspective view showing a suture loop attaching a piece of surgical mesh to a suture retaining washer.
Figure 15:
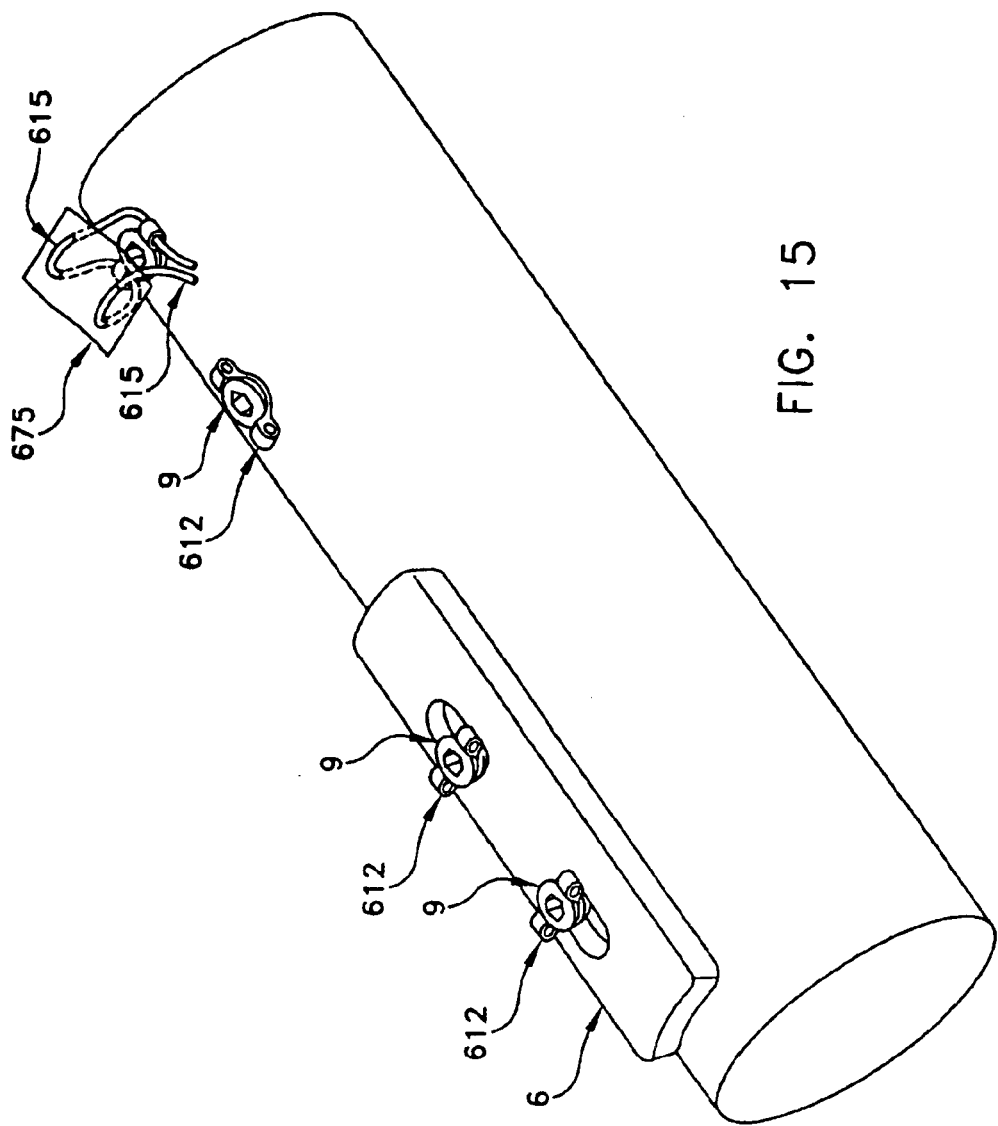
FIG. 15 is a view similar to that of FIG. 11, except showing the assembly of FIG. 14 secured to a bone.

If desired, suture loops 615 can be used to secure soft tissue to bone segments 20, 21. Alternatively, and looking next at FIGS. 14 and 15, suture loops 615 can be used to attach a surgical mesh 675 to bone segments 20, 21, or to attach other objects to bone segments 20, 21.

Figure 16:
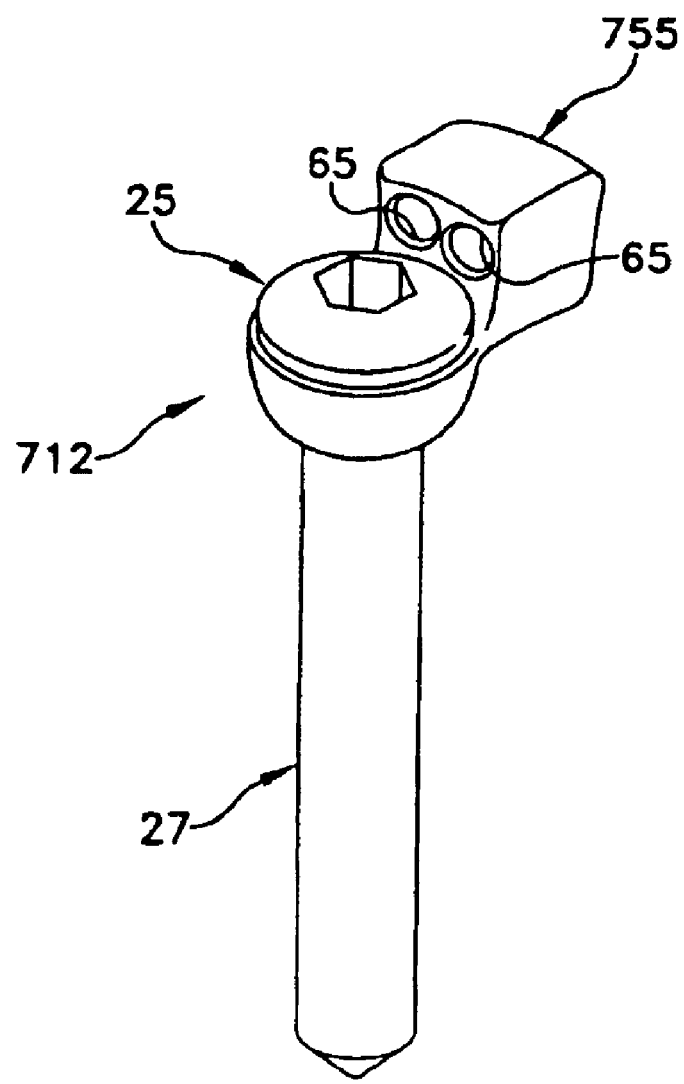
FIGS. 16–18 are schematic views showing another alternative form of cable retaining washer.
Figure 17:
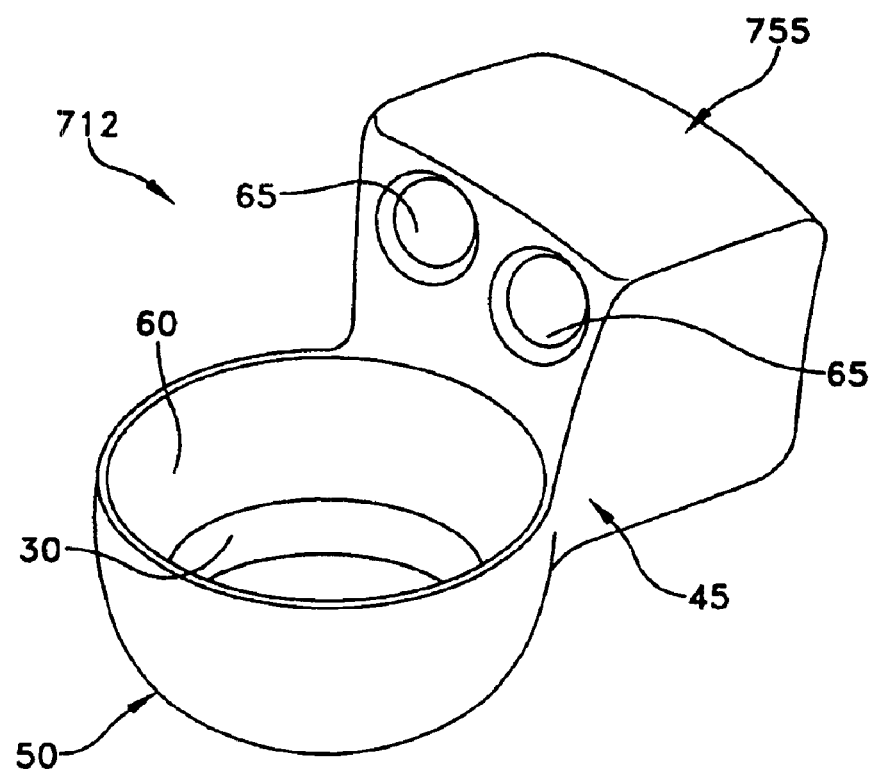
Figure 18:
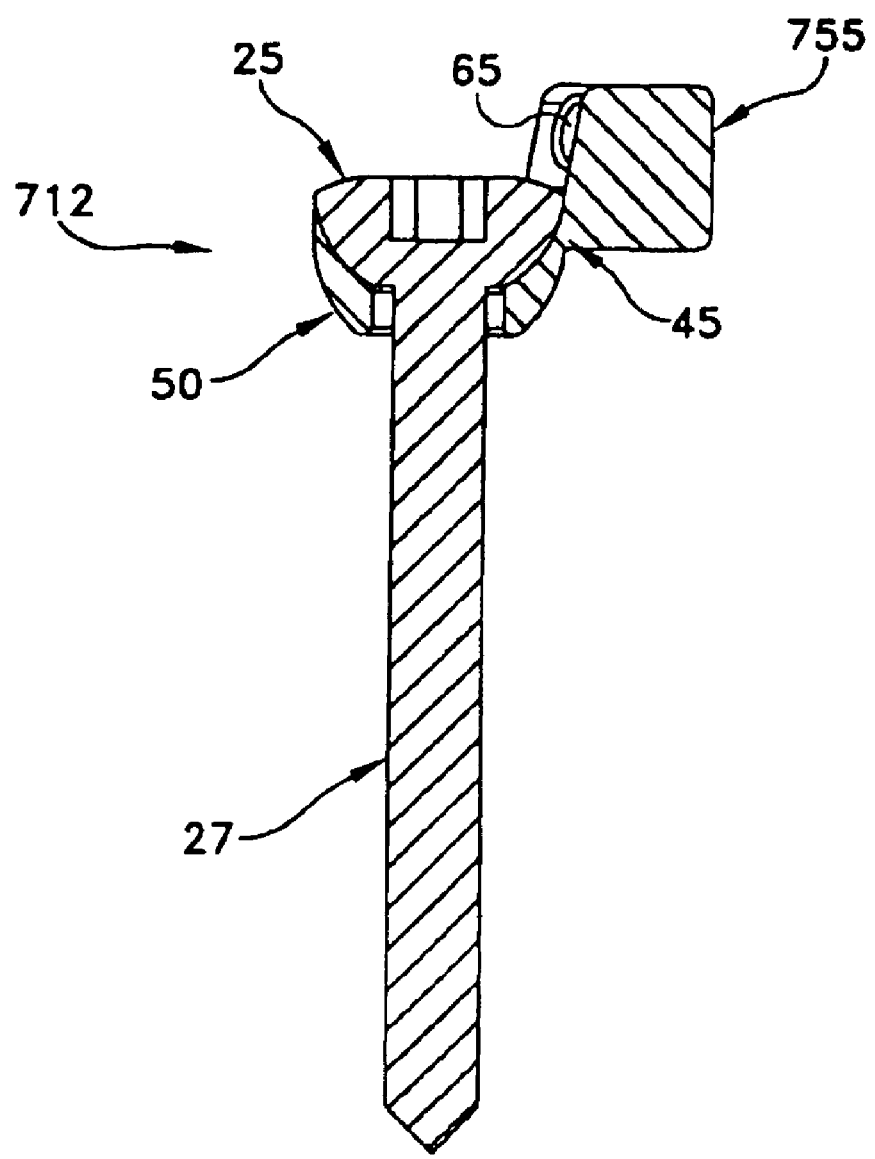

Looking next at FIGS. 16–18, there is shown a cable retaining washer 712 which comprises an alternative form of the invention. Cable retaining washer 712 is substantially the same as the cable retaining washer 212 described above, except that its upwardly projecting extension 755 has its one or more cable holes 65 extending along an axis substantially aligned with the head 25 of screw 9. Again, the upwardly projecting extension 755 may be crimped about a cable loop 15 extending through a cable hole 65.

Figure 19:
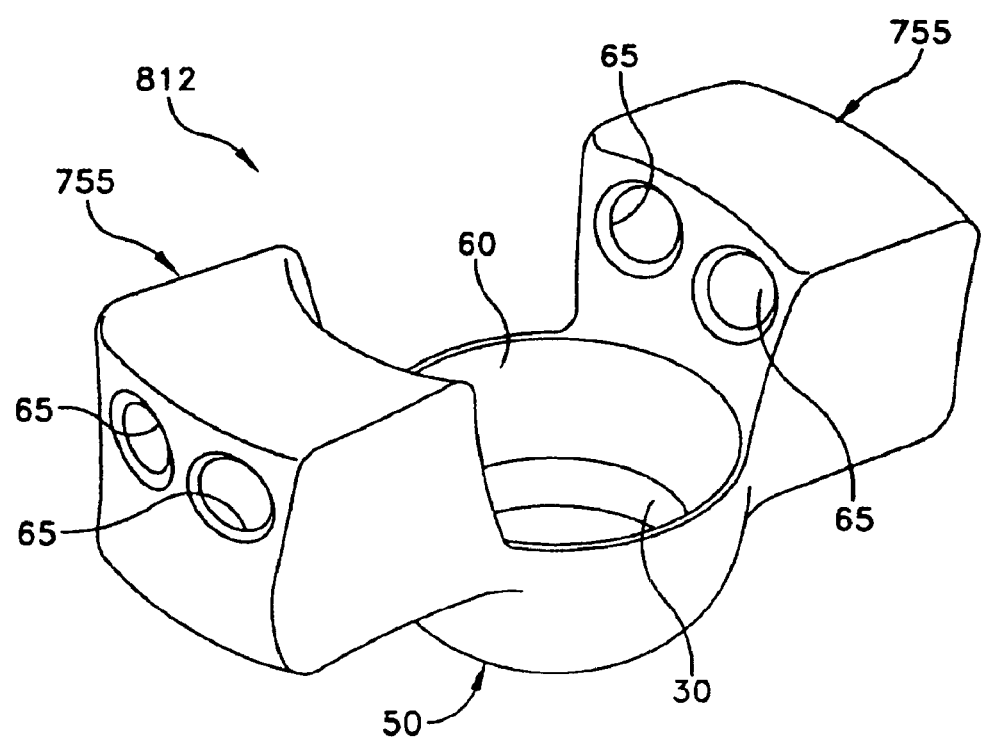
FIG. 19 is a schematic view showing another alternative form of cable retaining washer.

Looking next at FIG. 19, there is shown a cable retaining washer 812 which comprises another alternative form of the invention. Cable retaining washer 812 is substantially the same as the cable retaining washer 712 described above, except that it includes a second upwardly projecting extension 755 which also has its one or more cable holes 65 substantially aligned with the head 25 of screw 9. Again, the upwardly projecting extensions may be crimped about a cable loop 15 extending through a cable hole 65.

Figure 20:
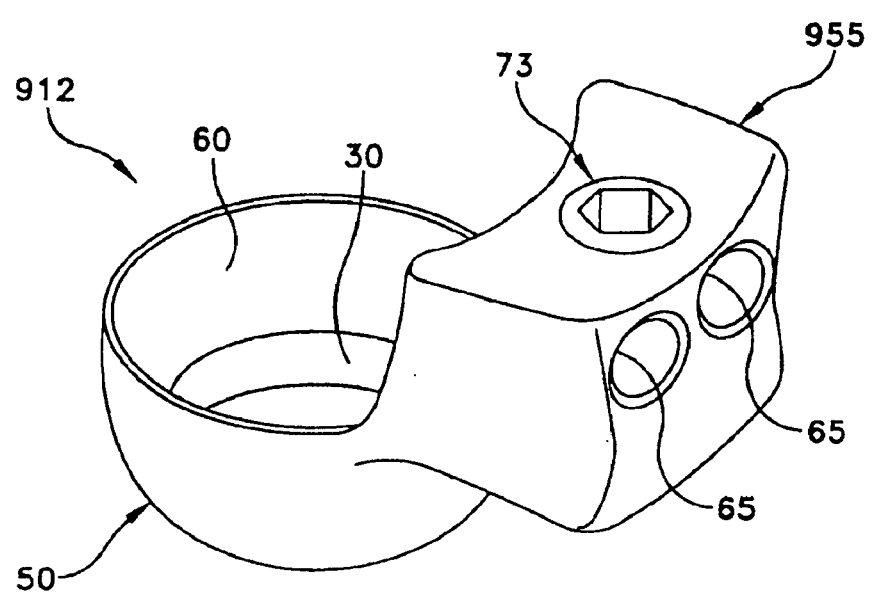
FIG. 20 is a schematic view showing still another alternative form of cable retaining washer.

Looking next at FIG. 20, there is shown a cable retaining washer 912 which comprises another alternative form of the invention. Cable retaining washer 912 is substantially the same as the cable retaining washer 12 described above, except that its upwardly projecting extension 955 has its one or more cable holes extending along an axis substantially aligned with the head 25 of screw 9. Again, set screw 73 may be tightened down so as to secure a cable loop 15 to the cable retaining washer.

Figure 21:
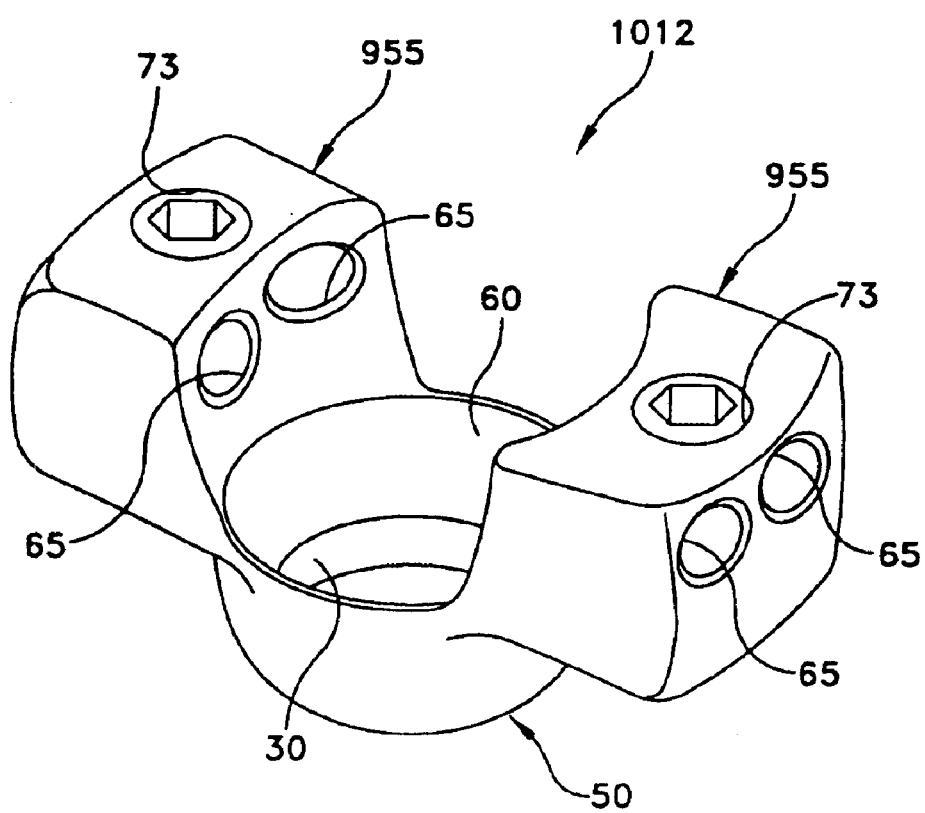
FIG. 21 is a schematic view of yet another form of cable retaining washer.

Looking next at FIG. 21, there is shown a cable retaining washer 1012 which comprises another alternative form of the invention. Cable retaining washer 1012 is substantially the same as the cable retaining washer 912 described above, except that it includes a second upwardly projecting extension 955 which also has its one or more cable holes 65 substantially aligned with the head 25 of screw 9. Again, a set screw 73 may be tightened down so as to secure a cable loop 15 to the cable retaining washer.

Figure 22:
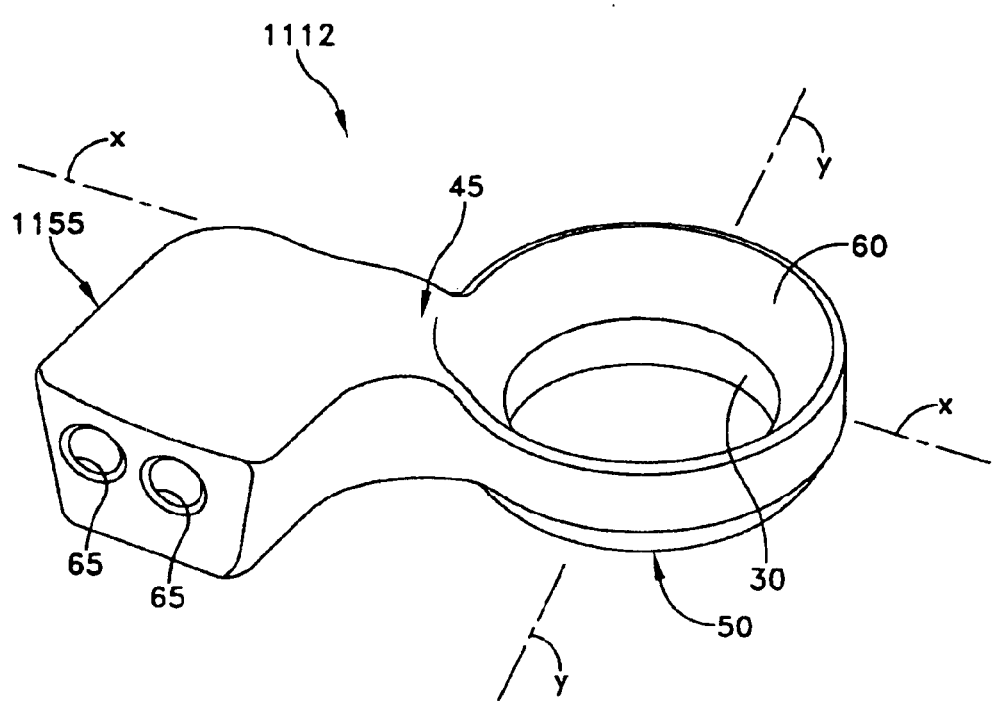
FIG. 22 is a schematic view of another form of cable retaining washer.

Looking next at FIG. 22, there is shown a cable retaining washer 1112 which comprises another alternative form of the invention. Cable retaining washer 1112 is substantially the same as the cable retaining washer 212 described above, except that the upwardly projecting extension 255 is replaced with a displaced extension 1155 having one or more cable holes 65 extending therethrough. More particularly, displaced extension 1155 is preferably formed in the same plane as body 45 and downwardly projecting extension 50, and is displaced both laterally (i.e., along the axis labeled "X" in FIG. 22) and longitudinally (i.e., along the axis labeled "Y" in FIG. 22) from downwardly projecting extension 50. By displacing extension 1155 laterally and longitudinally away from downwardly projecting extension 50, access to the extension 1155 with a crimping tool is enhanced.

Figure 23:
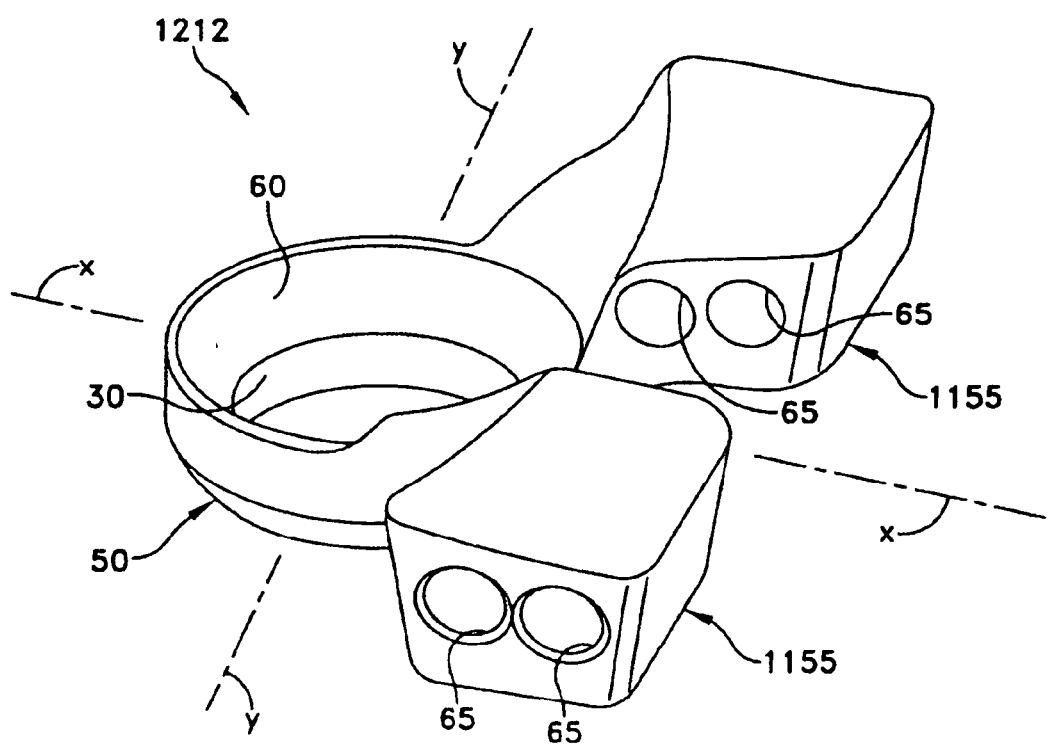
FIG. 23 is a schematic view of another form of cable retaining washer.

Looking next at FIG. 23, there is shown a cable retaining washer 1212 which comprises another alternative form of the invention. Cable retaining washer 1212 is substantially the same as the cable retaining washer discussed above, except that it includes a second displaced extension 1155. In one preferred embodiment, the one or more cable holes 65 of one displaced extension 1155 are aligned with the one or more cable holes 65 of the other displaced extension 1155. In another preferred embodiment, the two displaced extensions 1155 may be diametrically opposed from one another.

Figure 24:
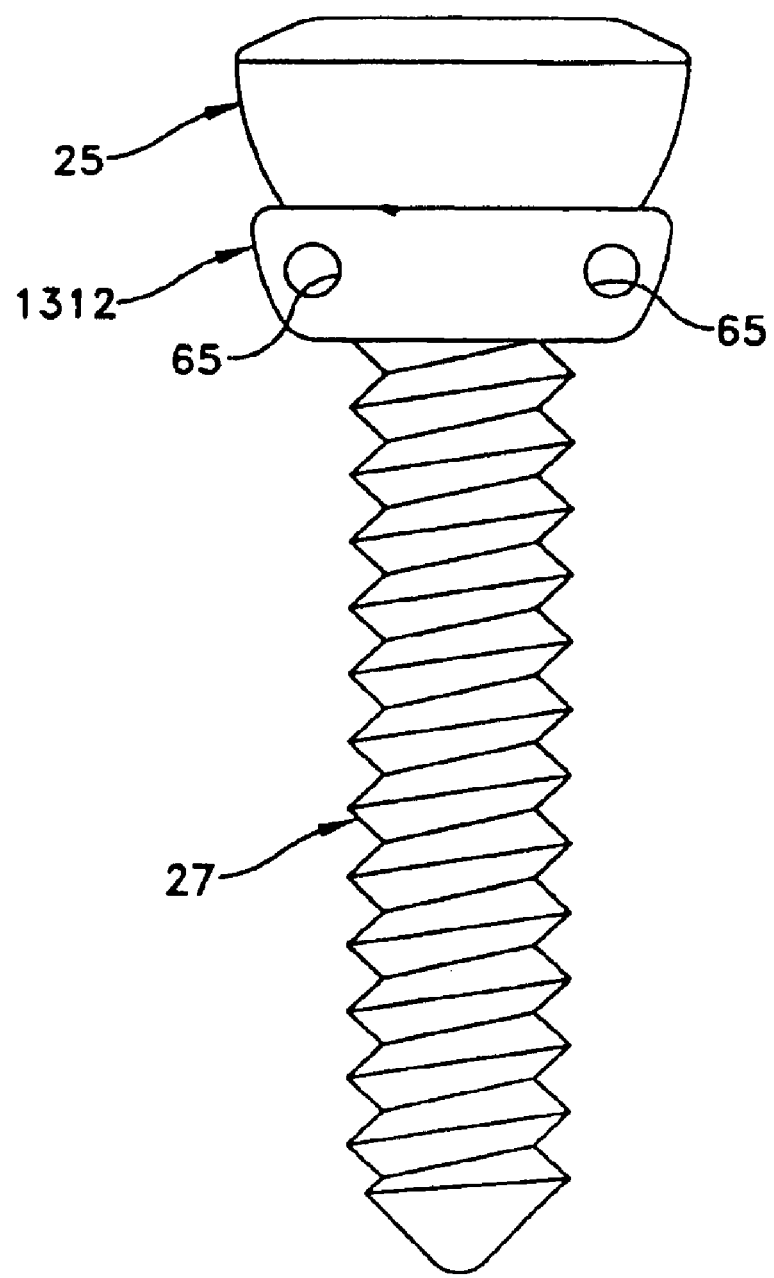
FIG. 24-26 are schematic views showing an alternative form of suture retaining washer.
Figure 25:
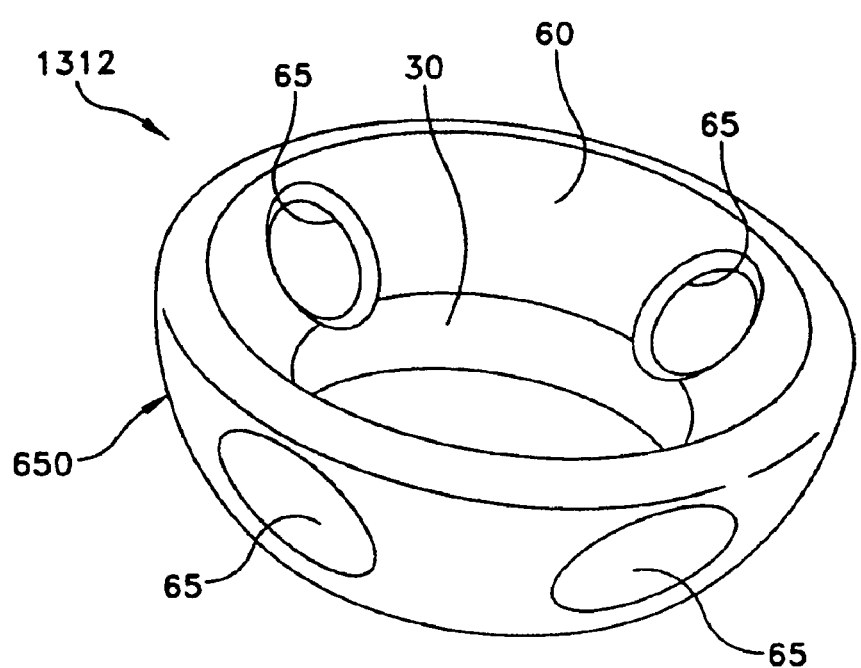
Figure 26:
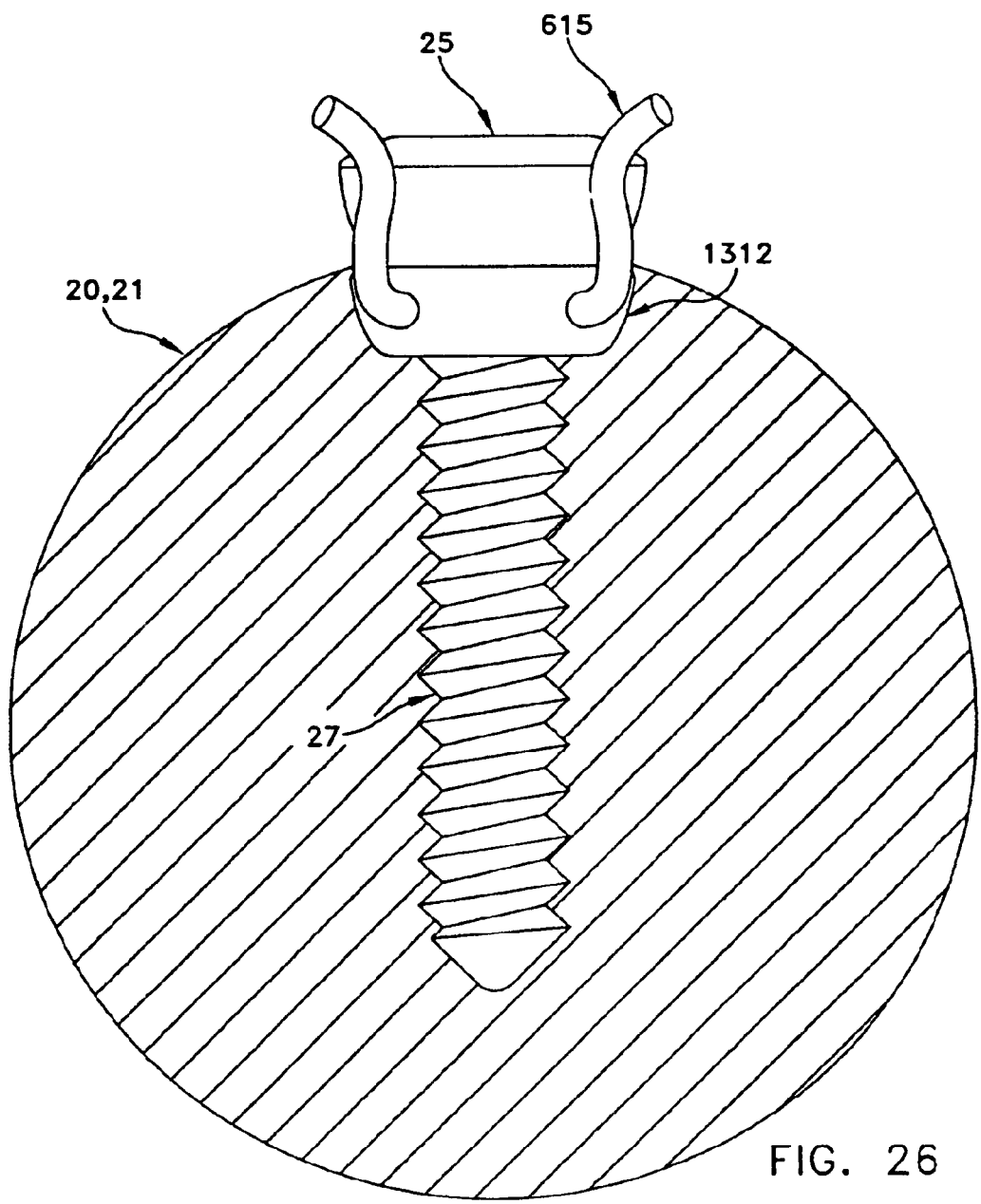

Looking next at FIGS. 24–26, there is shown a suture retaining washer 1312 which comprises another alternative form of the invention. Suture retaining washer 1312 is substantially the same as the suture retaining washer 612 described above, except that body 645 and upwardly projecting extensions 655 are omitted, and the at least one suture hole 65 is formed directly in the side wall of downwardly projecting extension 650. Preferably at least two suture holes 65 are provided, and the two suture holes are aligned with one another so as to receive a single suture loop 615 therethrough, such as is shown in FIG. 26. Preferably each suture hole 65 has its entrances and rounded somewhat so as to permit the suture to be slidingly adjusted therethrough prior to fully tightening down bone screw 9. However, suture retaining washer 1312 may, optionally, be constructed so that the head of the bone screw will lock the suture to the washer when the bone screw is fully tightened down. Suture retaining washer 1312 may be secured directly to a bore segment 20, 21 if desired, or it may be secured to a bone plate which is disposed between suture retaining washer 1312 and a bone segment 20, 21. Suture retaining washer 1312 is preferably formed so that it has a diameter substantially the same as the head of a bone screw 9 passing therethrough, so that the washer can fit beneath the head of the bone screw and thereby present a minimal peripheral profile.

What is claimed is:

1. A filament retaining washer for mounting about the shank of a bone screw deployed in a bone whereby to retain the filament to the bone, said filament retaining washer comprising:
a structure having a screw hole extending therethrough for receiving therein the shank of the bone screw deployed in the bone, whereby to secure said structure to said bone, said screw hole defining a first axis, and said structure having a filament hole extending therethrough for receiving a filament therein so as to retain said filament to said structure, said filament hole defining a second axis extending substantially perpendicular to said first axis, with said second axis being aligned with a bone screw extending through the screw hole, said structure having a top surface and a bottom surface, a portion of said bottom surface of said structure having a downwardly extending projection adapted to engage a top surface of a bone plate, and a downwardly extending projection adapted to seat in a recess formed in the top surface of the bone plate.

2. A filament retaining washer for mounting about the shank of a bone screw deployed in a bone whereby to retain the filament to the bone, said filament retaining washer comprising:
a body;
a downwardly projecting extension connected to said body and having a screw hole extending therethrough for receiving therein the shank of the bone screw deployed in the bone, whereby to secure said downwardly projecting extension to said bone, said screw hole defining a first axis, said downwardly projecting extension having a top surface and a bottom surface, and said bottom surface of said downwardly projecting extension being adapted to engage a top surface of a bone plate; and
an upwardly projecting extension connected to said body and having a filament hole extending therethrough for receiving a filament therein so as to retain said filament to said upwardly projecting extension, said filament hole defining a second axis extending substantially perpendicular to said first axis, with said second axis being aligned with a bone screw extending through the screw hole.

3. The filament retaining washer of claim 2 wherein said bottom surface of said downwardly projecting extension has a semi-spherical configuration similar to the semi-spherical underside of the head of the bone screw so as to seat in a recess formed in the top surface of the bone plate.

4. The filament retaining washer of claim 2 wherein said body forms a recess aligned with said screw hole.

5. The filament retaining washer of claim 2 wherein the filament is a suture.

6. The filament retaining washer of claim 2 wherein the filament is a cable.

7. The filament retaining washer of claim 6 wherein said upwardly projecting extension is configurable so as to restrain the cable within said filament hole.

8. The filament retaining washer of claim 7 wherein said upwardly projecting extension contains a set screw hole communicating with said filament hole, and a set screw disposed in said set screw hole for selectively engaging said cable so as to lock said cable relative to said upwardly projecting extension.

9. The filament retaining washer of claim 7 wherein said upwardly projecting extension is crimpable.

10. The filament retaining washer of claim 9 wherein said crimpable upwardly projecting extension has a trapezoidal cross-section.

11. The filament retaining washer of claim 2 further comprising a second upwardly projecting extension connected to said body and having a filament hole extending therethrough.

12. The filament retaining washer of claim 2 wherein said downwardly projecting extension is configured to engage a corresponding recess formed in a bone plate so as to prevent rotation of said filament retaining washer relative to the bone plate.

13. The filament retaining washer of claim 6 wherein said cable is braided cable.

14. The filament retaining washer of claim 6 wherein said cable is wire.

15. A system for securing an object to a bone, said system comprising:
a bone screw;
a washer comprising:
a body;
a downwardly projecting extension connected to said body and having a screw hole extending therethrough for receiving therein the shank of said bone screw deployed in the bone, whereby to secure said downwardly projecting extension to said bone, said screw hole defining a first axis, with said first axis being aligned with a bone screw extending through the screw hole; and an upwardly projecting extension connected to said body and having a filament hole extending therethrough, for receiving a filament therein so as to retain said filament to said upwardly projecting extension, said filament hole defining a second axis extending substantially perpendicular to said first axis; and a filament received by said filament hole, said filament securing the object to said bone.

16. The system of claim 15 wherein said downwardly projecting extension has a semi-spherical configuration similar to the semi-spherical underside of the head of the bone screw.

17. The system of claim 15 wherein said body forms a recess aligned with said screw hole, said recess receiving the head of the bone screw.

18. The system of claim 15 wherein the filament is a suture.

19. The system of claim 15 wherein the filament is a cable.

20. The system of claim 19 wherein said upwardly projecting extension is configurable so as to restrain the cable within said filament hole.

21. The system of claim 20 wherein said upwardly projecting extension contains a set screw hole communicating with said filament hole, and a set screw disposed in said set screw hole for selectively engaging said cable so as to lock said cable relative to said upwardly projecting extension.

22. The system of claim 20 wherein said upwardly projecting extension is crimpable.

23. The system of claim 22 wherein said crimpable upwardly projecting extension has a trapezoidal cross-section.

24. The system of claim 15 further comprising a second upwardly projecting extension connected to said body and having a filament hole extending therethrough.

25. The system of claim 15 further comprising a bone plate having a hole extending therethrough, with the shank of said bone screw passing therethrough, and said filament retaining washer being secured about the shank of said bone screw, between said bone and the head of said bone screw.

26. The system of claim 18 wherein said suture holds a piece of mesh to the bone.

27. The system of claim 15 wherein said downwardly projecting extension is configured to engage a corresponding recess formed in a bone plate so as to prevent rotation of said filament retaining washer relative to the bone plate.

28. The system of claim 19 wherein said cable is braided cable.

29. The system of claim 19 wherein said cable is wire.

30. A method for securing an object to a bone, said method comprising: providing a screw, a filament and a suture retaining washer, said suture retaining washer comprising: a body; a downwardly projecting extension connected to said body and having a screw hole extending therethrough for receiving therein the shank of a bone screw deployed in the bone, whereby to secure said downwardly projecting extension to said bone, said screw hole defining a first axis; and an upwardly projecting extension connected to said body and having a filament hole extending therethrough for receiving a filament therein so as to retain said filament to said upwardly projecting extension, said filament hole defining a second axis extending substantially perpendicular to said first axis, with said second axis being aligned with a bone screw extending through the screw hole; securing said washer to the bone with said screw, with said filament extending through said filament hole; and using said filament to secure the object to the bone.

31. The method of claim 30 wherein said filament is a cable, and further comprising the step of locking said cable to said suture retaining washer.

32. The method of claim 30 wherein said filament is suture.

33. The method of claim 32 wherein said object is a piece of soft tissue.

34. The method of claim 32 wherein said object is a piece of mesh.

35. The method of claim 31 wherein the object is bone.

36. The method of claim 30 wherein said washer is secured to said bone so that said washer is countersunk into the bone.

37. A filament retaining washer for mounting about the shank of a bone screw deployed in a bone whereby to retain the filament to the bone, said filament retaining washer comprising:
a body;
a downwardly projecting extension connected to said body and having a screw hole extending therethrough for receiving therein the shank of the bone screw deployed in the bone, whereby to secure said downwardly projecting extension to said bone, said screw hole defining a first axis, said downwardly projecting extension having a top surface and a bottom surface, and said bottom surface of said downwardly projecting extension being adapted to engage a top surface of a bone plate; and
an upwardly projecting extension connected to said body and having a filament hole extending therethrough for receiving a filament therein so as to retain said filament to said upwardly projecting extension, said filament hole defining a second axis extending substantially perpendicular to said first axis, with said upwardly projecting extension being displaced laterally and longitudinally from said downwardly projecting extension.

38. A filament retaining washer for mounting about the shank of a bone screw deployed in a bone whereby to retain the filament to the bone, said filament retaining washer comprising: a structure having a screw hole extending therethrough for receiving therein the shank of the bone screw deployed in the bone, whereby to secure said structure to said bone, said screw hole defining a first axis, and said structure having a filament hole so as to retain said filament to said structure, said filament hole defining a second axis extending substantially perpendicular to said first axis, with said second axis extending parallel to a third axis extending through said first axis, said structure having a top surface and a bottom surface, and said bottom surface of said structure having a downwardly extending projection adapted to engage a top surface of a bone plate having a recess formed therein.

39. A filament retaining washer according to claim 38 wherein said screw hole comprises a spherical recess about said top surface of said structure for receiving therein the underside of the head of a bone screw whose shank passes through the screw hole.

40. A filament retaining washer according to claim 38 wherein said washer has a diameter substantially the same as the head of a bone screw whose shank is sized to pass through the screw hole.

41. A filament retaining washer according to claim 38 wherein said filament hole comprises a pair of openings extending through said structure, wherein said pair of openings are aligned with one another along said second axis.

42. A filament retaining washer according to claim 38 wherein said filament hole is configured so that a filament extending therethrough will be locked to the washer when a bone screw extending through the screw hole is fully tightened down.

43. A filament retaining washer according to claim 38 wherein said filament hole is configured so that a filament extending therethrough will be movable relative to the washer when a bone screw extending through the screw hole is fully tightened down.

44. A filament retaining washer for mounting about the shank of a bone screw deployed in a bone whereby to retain the filament to the bone, said filament retaining washer comprising:

a body;

a downwardly projecting extension connected to said body and having a screw hole extending therethrough for receiving therein the shank of the bone screw deployed in the bone, whereby to secure said downwardly projecting extension to said bone, said screw hole defining a first axis; and an upwardly projecting extension connected to said body and having a filament hole extending therethrough for receiving a filament therein so as to retain said filament to said upwardly projecting extension, said filament hole defining a second axis extending substantially perpendicular to said first axis, with said second axis being aligned with a bone screw extending through the screw hole;

wherein said downwardly projecting extension is configured to engage a corresponding recess formed in a bone plate so as to prevent rotation of said filament retaining washer relative to the bone plate.

* * * * *

UNITED STATES PATENT AND TRADEMARK OFFICE
CERTIFICATE OF CORRECTION

| | | |
|---|---|---|
| PATENT NO. | : 6,960,213 B2 | Page 1 of 1 |
| APPLICATION NO. | : 09/981927 | |
| DATED | : November 1, 2005 | |
| INVENTOR(S) | : T. Wade Fallin et al. | |

It is certified that error appears in the above-identified patent and that said Letters Patent is hereby corrected as shown below:

Column 6. Line 39 (detailed description) DELET [[holes(s)]] and ADD --hole(s)--

Signed and Sealed this

Seventeenth Day of October, 2006

JON W. DUDAS
*Director of the United States Patent and Trademark Office*